US00PP26855P3

(12) United States Plant Patent
Eggleton

(10) Patent No.: US PP26,855 P3
(45) Date of Patent: Jun. 21, 2016

(54) ***VIOLA* PLANT NAMED 'SMEV5'**

(50) Latin Name: *Viola×hybrida*
Varietal Denomination: SMEV5

(71) Applicant: Steve Eggleton, Wonga Park (AU)

(72) Inventor: Steve Eggleton, Wonga Park (AU)

( * ) Notice: Subject to any disclaimer, the term of this patent is extended or adjusted under 35 U.S.C. 154(b) by 111 days.

(21) Appl. No.: 14/121,334

(22) Filed: Aug. 21, 2014

(65) Prior Publication Data

US 2016/0057915 P1 Feb. 25, 2016

(51) Int. Cl.
*A01H 5/02* (2006.01)

(52) U.S. Cl.
USPC ..... Plt./323

(58) Field of Classification Search
USPC ..... Plt./323
See application file for complete search history.

*Primary Examiner* — Susan McCormick Ewoldt
(74) *Attorney, Agent, or Firm* — Barbara Campbell; Bethany R. Roahrig; Cochran Freund & Young, LLC

(57) ABSTRACT

A new variety of *Viola* plant named 'SMEV5' that is distinguishable by compact dome-shaped habit, fragrant violet colored flowers consisting of dark violet upper petals and violet lateral and lower petals which exhibit prominent dark violet veins, flowers having a small bright yellow eye, hardy in USDA Zone 5, and blooms from early spring through fall, is disclosed.

2 Drawing Sheets

Genus and species: *Viola×hybrida*.
Variety denomination: 'SMEV5'.

BACKGROUND OF THE NEW PLANT

The present invention relates to a new and distinct cultivar of *Viola* known commonly as violet and grown for use in border, container, and landscape. The new invention from the family Violaceae is known botanically as *Viola×hybrida* and will be referred to hereinafter by the variety name 'SMEV5'.

'SMEV5' resulted from a formal breeding program conducted in Wonga Park, Victoria, Australia with the goal of producing a series of perennial *Viola* exhibiting a range of flower colors borne on plants with a uniform dense domed habit. The breeding program commenced in 2001.

'SMEV5' is a hybrid seedling selection that resulted from the controlled cross-pollination in December 2006 of the female parent, *Viola* 'Tiger Eyes' (unpatented) and the male parent, *Viola* 'Lord Primrose' (U.S. Plant Pat. No. 18,253). The resulting seed was collected, sown and raised to flowering during 2007. From approximately 150 seedlings, ten were selected and then propagated asexually by cuttings. From these ten, 'SMEV5' was selected in March 2008 based on the criteria of novel flower color and prolific flower number.

The unique traits exhibited by 'SMEV5' are compact dome-shaped habit, glossy green foliage, and numerous scented violet flowers, with a bright yellow eye. Blooming commences in early spring and continues through fall. After six months of growth from a rooted cutting the dimensions of 'SMEV5' are 20 cm in height and 20 cm in width. 'SMEV5' grows and flowers well under a wide range of conditions provided that the planting medium is maintained in moist condition. 'SMEV5' is hardy in USDA Zone 5.

The first asexual reproduction of 'SMEV5' was accomplished in 2008 in a cultivated area of Victoria, Australia. Asexual propagation was accomplished using the method of softwood cuttings. Since that time 'SMEV5' has been determined stable and true to type in subsequent generations of asexual propagation via softwood cuttings.

SUMMARY

The following traits have been repeatedly observed and represent the distinguishing characteristics of the new *Viola* variety named 'SMEV5'. 'SMEV5' has not been tested under all possible conditions and phenotypic differences may be observed with variations in environmental, climatic, and cultural conditions, however, without any variance in genotype.

1. 'SMEV5' exhibits compact dome-shaped habit.
2. 'SMEV5' exhibits green glossy foliage.
3. 'SMEV5' produces numerous flowers on short peduncles.
4. The flowers of 'SMEV5' are violet in color, consisting of dark violet upper petals and violet lateral and lower petals.
5. The lateral and lower petals of 'SMEV5' exhibit prominent dark violet veins.
6. The flowers of 'SMEV5' exhibit a small but distinct bright yellow eye.
7. The flowers of 'SMEV5' are pleasantly fragrant with the characteristic perfume of violets.
8. After one year of growth from a rooted cutting, 'SMEV5' is 20 cm in height including the flowers, and 20 cm in width.
9. 'SMEV5' is hardy in USDA Zone 5.
10. 'SMEV5' blooms from early spring through fall.

DESCRIPTION OF THE PHOTOGRAPHS

The accompanying color photographs illustrate the overall appearance of the new *Viola* variety named 'SMEV5' showing colors as true as is reasonably possible to obtain in color reproductions of this type. Colors in the photographs may differ from the color values cited in the detailed botanical description, which accurately describe the actual color of the new variety 'SMEV5'. Both photographs were made from a plant which has been grown in an unheated greenhouse in Arroyo Grande, Calif. No pinching or chemical growth regulators have been employed. Both photographs were made using conventional techniques and although flower and foliage color may appear different from actual color due to light reflectance, they are as accurate as possible by conventional photography.

DESCRIPTION OF THE NEW VARIETY

Figure 1:
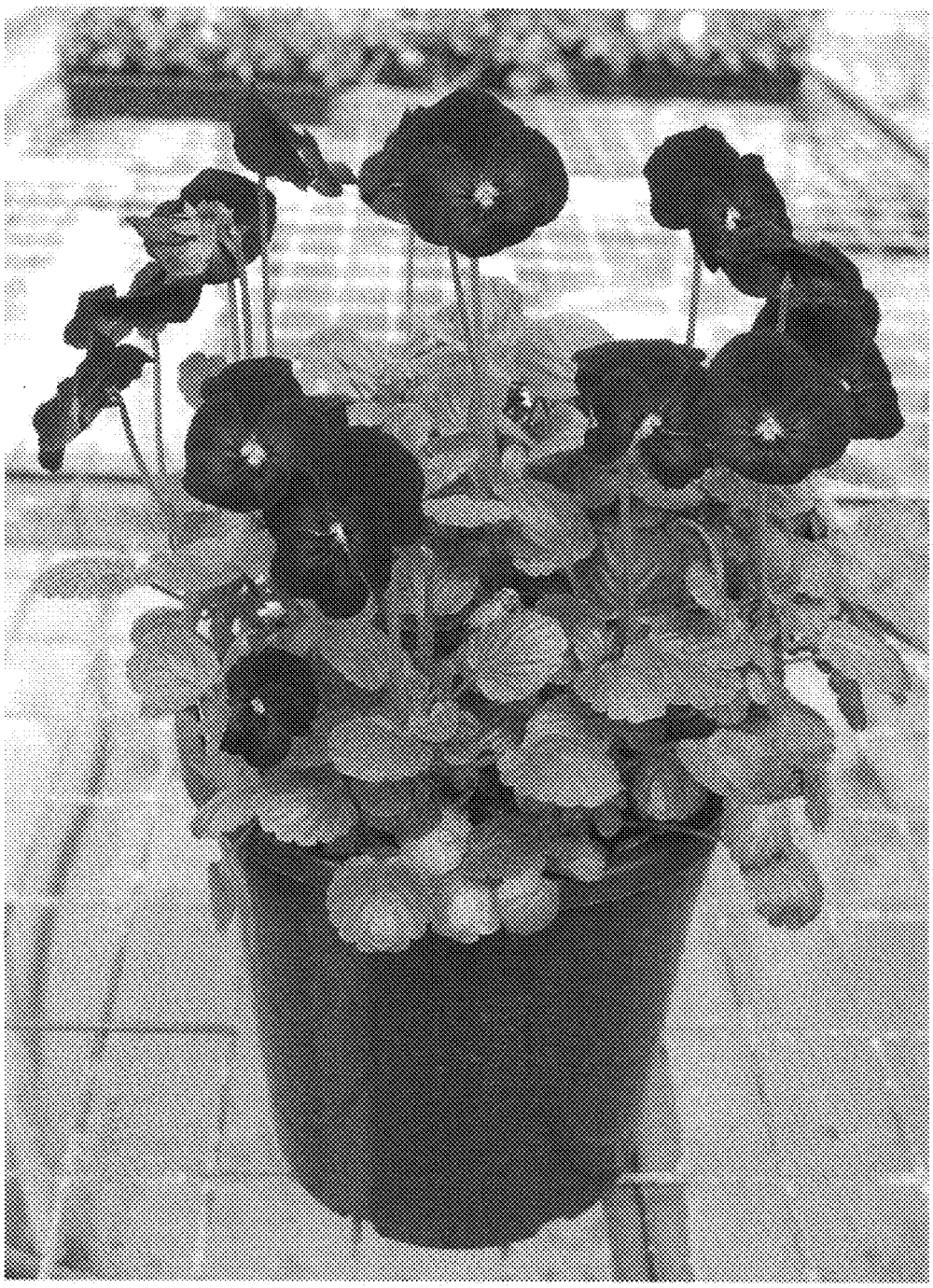
FIG. 1 depicts a 7-month-old plant in its first season of bloom in a 15 cm diameter container.
Figure 2:
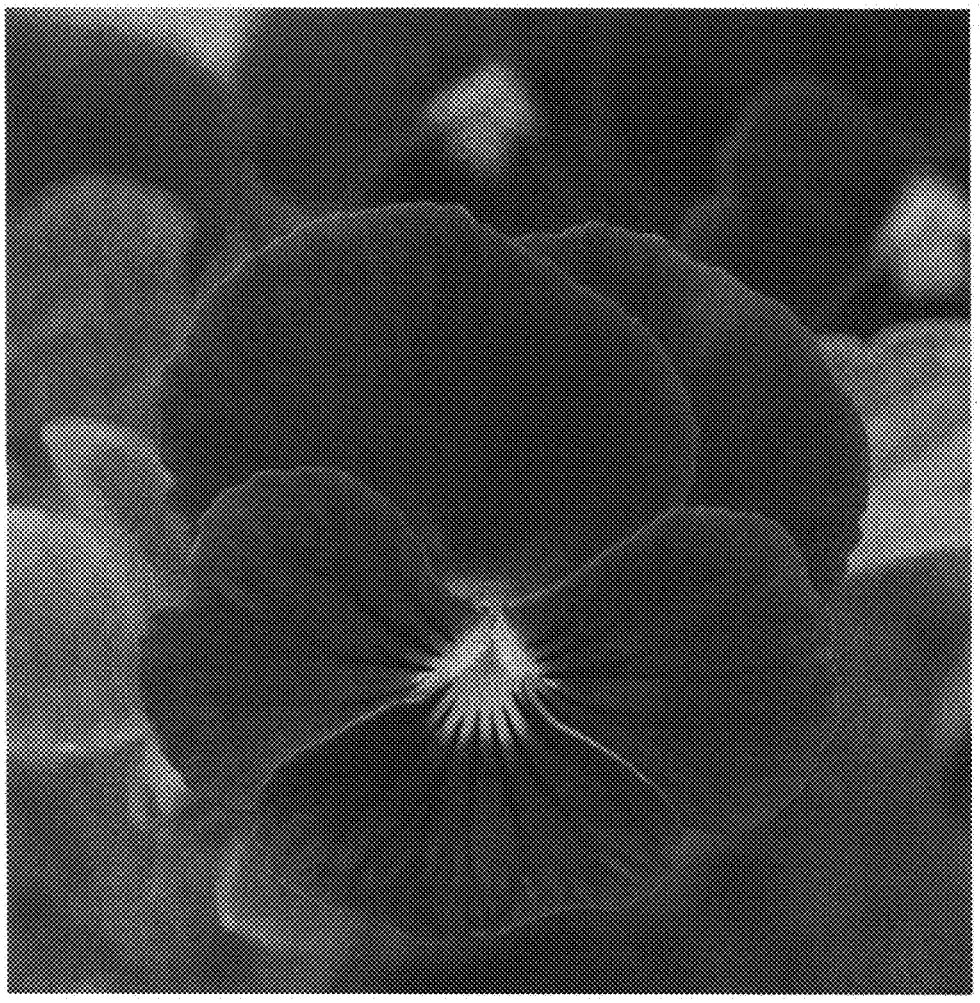
FIG. 2 depicts a close-up view of a flower on the plant shown in FIG. 1.

The following is a detailed botanical description of the new *Viola* variety named 'SMEV5'. Observations and measurements were collected from a six-month-old plant which had been grown in an unheated greenhouse in Arroyo Grande, Calif. Color determinations were made in accordance with The 2007 edition of The Royal Horticultural Society Colour Chart from London, England, except where general color terms of ordinary dictionary significance are used.

Botanical classification:

*Family*.—Violaceae.
*Genus*.—*Viola*.
*Species*.—×*hybrida*.
*Denomination*.—'SMEV5'.
*Common name*.—Violet.

Parentage:

*General*.—*Viola*×*hybrida* 'SMEV5' is a hybrid seedling selection that resulted from the controlled cross-pollination of the following parents.
*Female parent*.—*Viola* 'Tiger Eyes' (unpatented).
*Male parent*.—*Viola* 'Lord Primrose' (U.S. Plant Pat. No. 18,253).

Plant:

*Habit*.—Compact.
*Shape*.—Dome-shaped.
*Type*.—Perennial.
*Commercial category*.—Ornamental.
*Use*.—Border, container, and in the landscape.
*Suggested commercial containers*.—From multi-section bedding plant packs up to 1 gallon containers.
*Propagation method*.—Softwood cuttings.
*Rooting system*.—Fine and fibrous.
*Vigor*.—Moderate.
*Time to develop roots* (*range*).—14 to 20 days to develop roots on an initial cutting.
*Temperature to develop roots*.—The recommended air temperature is 20-21° Centigrade.
*Crop time* (*range*).—Under summer growing conditions, 'SMEV5' will flower and be saleable in a 10 cm container in flower after 3 months of growing from an unrooted cutting. During winter and spring months in an unheated greenhouse 'SMEV5' flowers and is saleable in 4 to 6 months depending on light levels and day length.
*Plant dimensions*.—20 cm in height including the flowers, and 20 cm in width.
*Cultural requirements*.—Consistently moist soil or container medium.
*Pest or disease resistance or susceptibility*.—No particular disease or pest resistance or susceptibility is known to the inventor.
*Hardiness*.—USDA Zone 5.

Stem:

*Branching*.—Basal.
*Stem color*.—N144C.
*Stem length* (*average*).—5 cm.
*Stem width*.—0.25 cm.
*Stem shape*.—Cylindrical.
*Stem surface*.—Glabrous.
*Internode* (*average*).—0.75 cm.

Foliage:

*Type*.—Evergreen.
*Leaf arrangement*.—Alternate.
*Leaf division*.—Simple.
*Leaf quantity*.—Approximately 12 to 16 per stem.
*Margin*.—Crenate.
*Leaf shape*.—Ovate.
*Leaf length* (*range*).—2.0 cm to 3.50 cm.
*Leaf width* (*range*).—1.50 cm to 2.25 cm.
*Leaf color* (*abaxial surface*).—137C.
*Leaf color* (*adaxial surface*).—137A.
*Leaf base*.—Rounded.
*Leaf apex*.—Rounded.
*Venation*.—Pinnate.
*Vein color* (*abaxial and adaxial surfaces*).—137C.
*Leaf surface* (*abaxial and adaxial*).—Glabrous.
*Leaf attachment*.—Petiolate.
*Petiole color*.—138B.
*Petiole dimensions*.—1 to 2 cm in length and 1 mm in width.
*Petiole shape*.—Sulcate.
*Petiole surface*.—Glabrous.

Inflorescence:

*Inflorescence*.—Solitary terminal flower consisting of five petals.
*Inflorescence quantity*.—Approximately 10 open and opening flowers.
*Aspect* (*range*).—Facing outward to pendant when aging.
*Inflorescence width*.—3.5 cm.
*Inflorescence length*.—4.0 cm.
*Inflorescence depth*.—2.0 cm.
*Inflorescence shape*.—Rotate.
*Blooming seasons*.—Early spring through fall.
*Peduncle length* (*range*).—5.50 cm to 7 cm.
*Peduncle width*.—3 mm.
*Peduncle shape*.—Sub-cylindrical.
*Peduncle surface*.—Glabrous.
*Peduncle color*.—144B.
*Peduncle strength*.—Flexible.
*Bud color*.—143B.
*Bud shape*.—Elongated oval.
*Bud dimensions* (*average*).—1.30 cm in length and 0.40 cm in width.
*Bud surface*.—Glabrous.
*Bud apex*.—Rounded.
*Corolla tube depth*.—6 mm.
*Petal quantity*.—5, consisting of 2 upper petals, 2 lateral petals, and 1 lower petal.
*Upper petals* (*two*).—Petal shape: Reniform. Petals fused or unfused: Unfused. Petal apex: Rounded. Petal base: Truncate to cuneate. Petal margin: Entire, lightly undulating. Petal length: 1.5 cm to 2.0 cm. Petal width: 2.0 cm to 2.5 cm. Petal color (both surfaces): Predominantly 79A, becoming lighter 77A towards margin and base. Veins: 79A but barely evident. Petal surface (both surfaces): Glabrous.

*Lateral petals* (*two*).—Petal shape: Reniform. Petals fused or unfused: Fused. Petal apex: Rounded. Petal base: Truncate. Petal margin: Entire, lightly undulating. Petal length: 1.2 cm to 1.5 cm. Petal width: 1.5 cm to 1.8 cm. Petal color (adaxial surface): 93B with orange red iridescence, color difficult to match, appears close to 42C. Petal color (abaxial surface): 93B. Veins (adaxial surface only): Approximately 8 in number, parallel at base then diverging, length between 0.5 cm and 1.2 cm, width up to 2 mm. Vein color 79A. Petal surface (both surfaces): Glabrous.

*Lower petal* (*one*).—Petal shape: Obcordate. Petals fused or unfused: Fused. Petal apex: Emarginate. Fully developed petal exhibits notch, depth 0.3 cm to 0.4 cm. Petal base: Truncate. Petal margin: Entire, lightly undulating. Petal length: 1.5 cm to 1.7 cm. Petal width: 2.0 cm to 2.2 cm. Petal color (adaxial surface): 93B (outer one-third of ground) with iridescence close to 42C extending towards base. Lower ground and base bright mid-yellow 14B, creating the petal "eye". Petal color (abaxial surface): 93B. Veins (adaxial surface only): Approximately 8 in number, parallel towards base then diverging, length between 0.5 cm and 1.0 cm, width up to 3 mm. Vein color: 79A; veins disappear abruptly within the mid-yellow eye. Petal surface (both surfaces): Glabrous.

*Calyx shape*.—Stellate.

*Calyx diameter*.—2 cm.

*Sepals*.—5 in number.

*Sepal dimensions*.—1 cm in length and 0.40 cm in width.

*Fused or unfused*.—Sepals unfused.

*Sepal color* (*both surfaces*).—138A.

*Sepal apex*.—Acute.

*Sepal base*.—Truncate.

*Sepal surface*.—Glabrous.

*Sepal margin*.—Entire.

*Sepal shape*.—Lanceolate.

*Inflorescence self-cleaning or persistent*.—Self-cleaning.

*Inflorescence fragrance*.—Pleasant scent characteristic of violets.

*Lastingness of inflorescence* (*range*).—5 to 7 days.

Reproductive organs:

*Stamen quantity*.—5 joined around ovary.

*Stamen length*.—4 mm.

*Stamen color*.—145D.

*Anther length*.—Less than 1 mm.

*Anther width*.—2.50 mm.

*Anther color*.—164A.

*Pollen color*.—155C.

*Pollen quantity* (*range*).—Moderate to heavy.

*Pistil quantity*.—1.

*Pistil height*.—6.5 mm.

*Style height*.—1 mm.

*Style color*.—N144A.

*Stigma dimensions*.—Less than 1 mm in height and 1 mm in diameter.

*Stigma color*.—N144A.

*Stigma shape*.—Globular.

*Stigma surface*.—Glandular.

*Ovary position*.—Superior.

*Ovary color*.—N144A.

*Ovary shape*.—Dome-shaped.

*Ovary dimensions*.—6 mm in height and 3 mm in width.

Seed: None observed to date.

COMPARISON TO PARENTAL VARIETY AND COMMERCIAL VARIETIES

'SMEV5' is distinguishable from each of its parents by flower color as follows. The flowers of 'SMEV5' are predominantly violet in color, consisting of dark violet upper petals and violet lateral and lower petals. In addition, the lateral and lower petals of 'SMEV5' exhibit dark violet veins. The flowers of 'SMEV5' exhibit a small but distinct bright yellow eye. The flowers of the female parent, *Viola* 'Tiger Eyes' (unpatented), are golden yellow throughout except for a dark brown to black central blotch and radiating veins. The flowers of the male parent, *Viola* 'Lord Primrose' (U.S. Plant Pat. No. 18,253) are bicolored pale violet and mid yellow, without a prominent eye.

The closest comparison plant in commerce known to the inventor is the male parent, *Viola* 'Lord Primrose' (U.S. Plant Pat. No. 18,253). The flowers of 'SMEV5' are predominantly violet in color, consisting of dark violet upper petals and violet lateral and lower petals. In addition, the lateral and lower petals of 'SMEV5' exhibit dark violet veins. The flowers of 'SMEV5' exhibit a small but distinct bright yellow eye. The flowers of the male parent, *Viola* 'Lord Primrose' (U.S. Plant Pat. No. 18,253) are bicolored pale violet and mid yellow, without a prominent eye.

'SMEV5' may be compared with the inventor's varieties of *Viola* plants named 'SMEV4' (U.S. Plant Pat. No. 24,591) and 'SMEV3' (U.S. Plant Pat. No. 24,592) both of which, together with the instant variety, were selected as seedlings from the same parental cross, namely 'Tiger Eyes' and 'Lord Primrose' (U.S. Plant Pat. No. 18,253).

Whereas 'SMEV4' bears tri-colored flowers (dark violet, mid violet and golden yellow) and 'SMEV3' bears bi-colored flowers (mauve-pink and yellow), the flowers of 'SMEV5' are violet in color, without any presence of yellow except for the small but distinct yellow eye. In addition, neither of the flowers of 'SMEV4' or 'SMEV3' exhibit a yellow eye.

I claim:

1. A new and distinct cultivar of *Viola* plant named 'SMEV5' as described and illustrated herein.

* * * * *